(12) United States Patent
Cumberbatch et al.

(10) Patent No.: US 8,188,053 B2
(45) Date of Patent: May 29, 2012

(54) ANTI-INFLAMMATORY PEPTIDES

(75) Inventors: Marie Cumberbatch, Manchester (GB); Rebecca Jane Dearman, Manchester (GB); Ian Kimber, Manchester (GB); Russell Colin Viner, Wokingham (GB)

(73) Assignee: The University of Manchester, Manchester (GB)

( * ) Notice: Subject to any disclaimer, the term of this patent is extended or adjusted under 35 U.S.C. 154(b) by 410 days.

(21) Appl. No.: 12/086,210

(22) PCT Filed: Dec. 4, 2006

(86) PCT No.: PCT/GB2006/004510
§ 371 (c)(1),
(2), (4) Date: Jun. 10, 2009

(87) PCT Pub. No.: WO2007/066081
PCT Pub. Date: Jun. 14, 2007

(65) Prior Publication Data
US 2009/0253631 A1    Oct. 8, 2009

(30) Foreign Application Priority Data
Dec. 6, 2005   (GB) .................................. 0524884.4

(51) Int. Cl.
| A61K 38/00 | (2006.01) |
| A61K 38/04 | (2006.01) |
| A61K 38/08 | (2006.01) |
| C07K 9/00  | (2006.01) |
| C07K 7/00  | (2006.01) |
| C07K 7/04  | (2006.01) |
| C07K 7/06  | (2006.01) |

(52) U.S. Cl. .................... 514/21.6; 514/21.8; 514/12.2; 530/300; 530/328; 530/330

(58) Field of Classification Search .................. None
See application file for complete search history.

(56) References Cited

U.S. PATENT DOCUMENTS
7,183,381 B2 * 2/2007 Varadhachary et al. ...... 530/350

FOREIGN PATENT DOCUMENTS
| EP | 1 616 948 | 1/2006 |
| WO | WO96/30397 | 10/1996 |
| WO | WO97/39023 | 10/1997 |
| WO | WO99/19347 | 4/1999 |
| WO | WO00/48622 | 8/2000 |
| WO | WO02/50289 | 6/2002 |
| WO | WO2007/066081 | 6/2007 |

OTHER PUBLICATIONS

Examination Report corresponding to European Patent Application No. EP 06 820 396.7 dated Jun. 7, 2010.
Office Action corresponding to Chinese PCT National Phase Patent Application No. 200680046198.0 dated Sep. 11, 2010.
Decision to Grant a European Patent corresponding to European Patent Application No. EP 06 820 396.7-2403 1960515 dated Apr. 21, 2011.
International Search Report corresponding to International Application No. PCT/GB2006/004510 dated Apr. 3, 2007.
Takashima et al., "New Technologies to Prevent and Treat Contact Hypersensitivity Responses," Annals of the New York Academy of Sciences. vol. 919 pp. 205-213 (2000).

* cited by examiner

*Primary Examiner* — Elizabeth C Kemmerer
(74) *Attorney, Agent, or Firm* — Jenkins, Wilson, Taylor & Hunt, P.A.

(57) ABSTRACT

The present invention relates, inter alia, to a method of ameliorating an inflammatory skin condition. Thus, the present invention provides a peptide that includes the amino acid sequence KMIKP (SEQ ID NO: 20), wherein the peptide includes no more than 70 amino acids and wherein the peptide is capable of inhibiting allergen induced Langerhans cell migration, and wherein the peptide is not that depicted in SEQ ID NO. 19. The present invention also relates to the use of a peptide that includes the amino acid sequence KMIKP (SEQ ID NO: 20), wherein the peptide includes no more than 100 amino acids, and wherein the peptide is capable of inhibiting allergen induced Langerhans cell migration, in the manufacture of a topical medicament for the treatment of an inflammatory skin condition.

13 Claims, 13 Drawing Sheets

SEQUENCE LISTING

```
<160> NUMBER OF SEQ ID NOS: 22

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 1

Val Lys Gln Ile Glu Ser Lys Thr Ala Phe Gln Glu Ala Leu Asp Ala
1               5                   10                  15

Ala Gly Asp Lys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Ala Ala Gly Asp Lys Leu Val Val Val Asp Phe Ser Ala Thr Trp Cys
1               5                   10                  15

Gly Pro Cys Lys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Cys Gly Pro Cys Lys Met Ile Lys Pro Phe Phe His Ser Leu Ser Glu
1               5                   10                  15
```

```
Lys Tyr Ser Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 4

Glu Lys Tyr Ser Asn Val Ile Phe Leu Glu Val Asp Val Asp Cys
1               5                   10                  15

Gln Asp Val Ala
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Cys Gln Asp Val Ala Ser Glu Cys Glu Val Lys Cys Met Pro Thr Phe
1               5                   10                  15

Gln Phe Phe Lys
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 6

Phe Gln Phe Phe Lys Lys Gly Gln Lys Val Gly Glu Phe Ser Gly Ala
1               5                   10                  15

Asn Lys Glu Lys
            20

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Ala Asn Lys Glu Lys Leu Glu Ala Thr Ile Asn Glu Leu Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide

<400> SEQUENCE: 8

Ser Ala Thr Tyr Cys Gly Pro Cys Lys Met Ile Lys Pro
1               5                   10

<210> SEQ ID NO 9
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 9

Cys Gly Pro Cys Lys Met Ile Lys Pro
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Ile Pro Cys Met Pro Lys Cys Lys Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Ala Gly Pro Ala Lys Met Ile Lys Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Ile Pro Ala Met Pro Lys Ala Lys Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Syntehtic peptide

<400> SEQUENCE: 13

Lys Met Ile Pro Lys
1               5

<210> SEQ ID NO 14
<211> LENGTH: 105
<212> TYPE: PRT
<213> ORGANISM: Homo sapiens

<400> SEQUENCE: 14

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
```

```
                50                  55                  60
Val Ala Ser Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Val
                100                 105
```

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

```
Lys Met Ile Lys Pro Phe Phe His Ser Leu Ser Glu Lys Tyr Ser Asn
 1               5                  10                  15
```

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

```
Cys Gly Pro Cys Lys Met Ile Lys Pro Phe Phe His Ser Leu Ser Glu
 1               5                  10                  15
```

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

```
Ala Gly Pro Ala Lys Met Ile Lys Pro Phe Phe His Ser Leu Ser Glu
 1               5                  10                  15

Lys Tyr Ser Asn
            20
```

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

```
Ser Ala Thr Tyr Cys Gly Pro Cys Lys Met Ile Lys Pro
 1               5                  10
```

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide

<400> SEQUENCE: 19

```
Trp Cys Gly Pro Cys Lys Met Ile Lys Pro Phe Phe
 1               5                  10
```

-continued

```
<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Lys Met Ile Lys Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Lys Met Ile Met Pro
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Cys Gly Pro Cys
1
```

ANTI-INFLAMMATORY PEPTIDES

Figure 1:
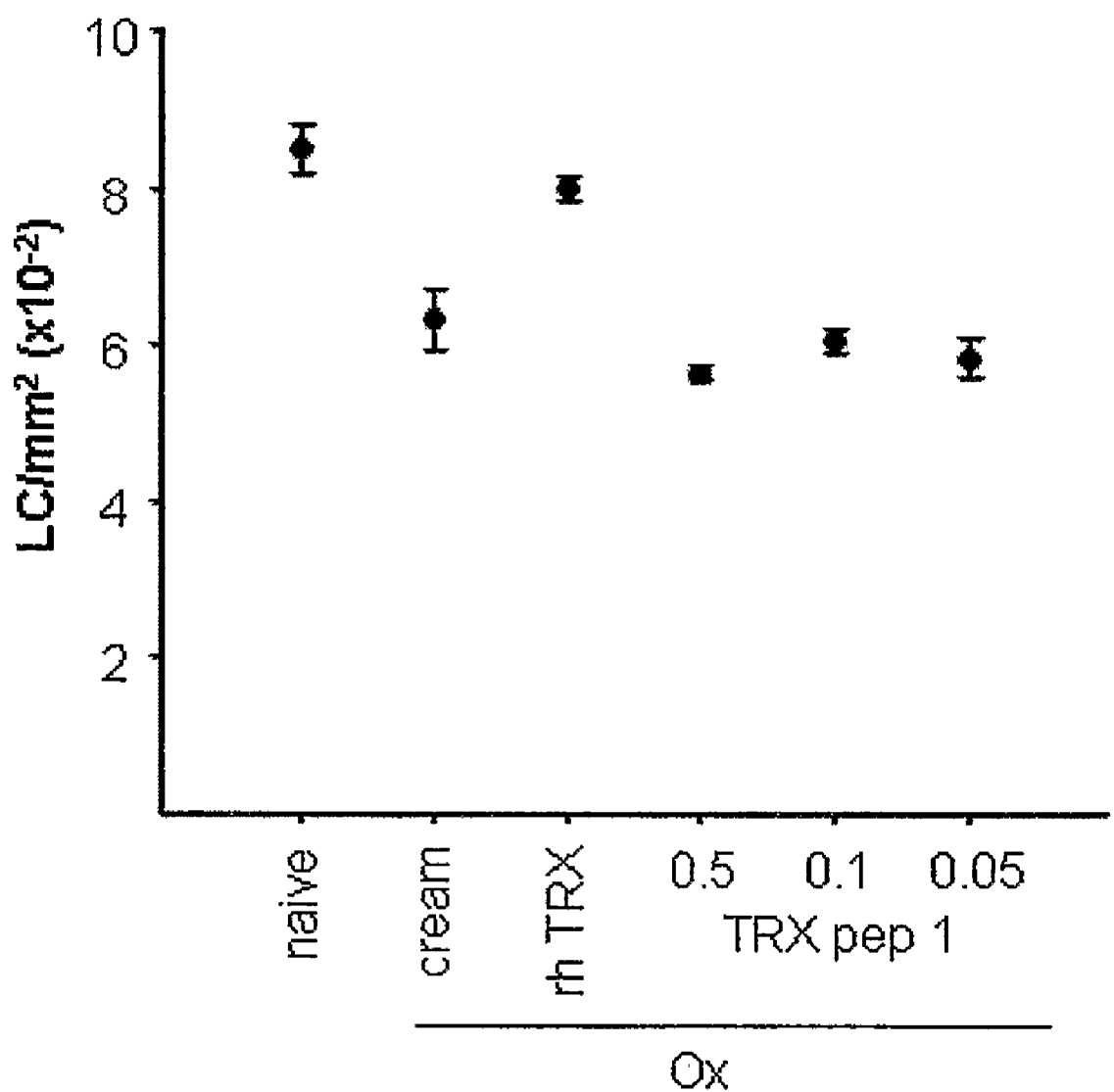

The present invention relates, inter alia, to a method of ameliorating an inflammatory skin condition. Inflammatory skin conditions are known to be associated with the altered expression of chemokines and cytokines, and in particular the increased activity of pro-inflammatory cytokines such as interleukin (IL)-1α, IL-1β and tumour necrosis factor α (TNF-α). These same cytokines are known also to play pivotal roles in the initiation of skin immune responses, and in fact provide mandatory signals for the migration of epidermal Langerhans cells (LC) from the skin. The movement of LC from the epidermis, and their subsequent accumulation in skin-draining lymph nodes provides a mechanism for the transport of antigen to the sites (regional lymph nodes) where primary immune responses are induced.

The present invention is based on the surprising discovery that certain thioredoxin-derived peptides are able to inhibit the migration of epidermal LC—consistent with perturbed proinflammatory cytokine expression—when applied topically to the skin.

Thus, according to the present invention there is provided a peptide comprising the amino acid sequence KMIKP (SEQ ID NO: 20), wherein the peptide comprises no more than 70 amino acids and wherein the peptide is capable of inhibiting allergen induced Langerhans cell migration, and wherein the peptide is not WCGPCKMIKPFF (SEQ ID NO: 19).

Preferably, the peptide of the present invention comprises no more than 60 or 50 or 40 or 30 or 20 or 10 amino acids. More preferably the peptide is selected from the group consisting of:

| | |
|---|---|
| CGPCKMIKPFFHSLSEKYSN; | (SEQ ID NO: 3) |
| KMIKPFFHSLSEKYSN; | (SEQ ID NO: 5) |
| CGPCKMIKPFFHSLSE; | (SEQ ID NO: 16) |
| AGPAKMIKPFFHSLSEKYSN; | (SEQ ID NO: 17) |
| SATYCGPCKMIKP; | (SEQ ID NO: 18) |
| CGPCKMIKP; | (SEQ ID NO: 9) |
| AGPAKMIKP; and | (SEQ ID NO: 11) |
| KMIKP | (SEQ ID NO. 20) |

The present invention further provides a pharmaceutical composition comprising a peptide according to the present invention. Preferably the pharmaceutical composition is selected from the group consisting of a solution, a gel, a lotion, an ointment, a cream and a paste.

The present invention still further relates to the use of a peptide according to the present invention as a pharmaceutical.

The present invention also relates to the use of a peptide comprising the amino acid sequence KMIKP (SEQ ID NO: 20), wherein the peptide comprises no more than 100 amino acids, and wherein the peptide is capable of inhibiting allergen induced Langerhans cell migration, in the manufacture of a topical medicament for the treatment of an inflammatory skin condition. Preferably, the inflammatory skin condition is selected from the group consisting of psoriasis, lichen planus, atopic eczema, irritant or allergic contact dermatitis, contact urticaria, infantile eczema and acne vulgaris.

The present invention further relates to a nucleic acid sequence encoding a polypeptide of the present invention.

The present invention still further relates to a method of manufacture of the peptide. Where appropriate, the peptide is manufactured by chemical synthesis using methods well known to the skilled person. For longer peptides, it is also possible that recombinant DNA technologies may be used to provide the peptides, again using methods well know to the skilled person.

The present invention further relates to a "conservative variant" of the peptide of the present invention. By "conservative variant" it is meant that one or more of the amino acids in the KMIKP (SEQ ID NO: 20) motif are substituted with an amino acid having similar properties—and wherein the biological activity of the peptide is substantially retained following the substitution.

LIST OF FIGURES

In all figures "OX"=oxazolone.

FIG. 1 Epidermal Langerhans cell migration—dose response experiment for peptide 1.

Figure 2:
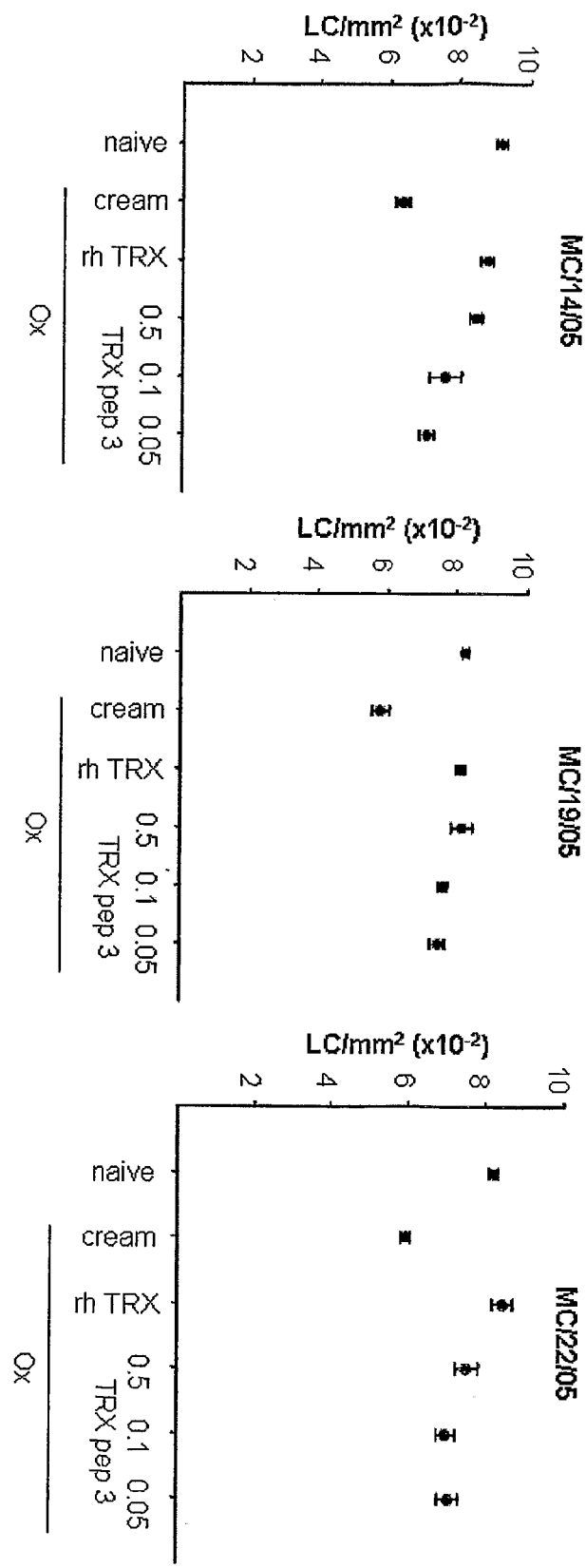

FIG. 2 Epidermal Langerhans cell migration—dose response experiment for peptide 3.

Figure 3:
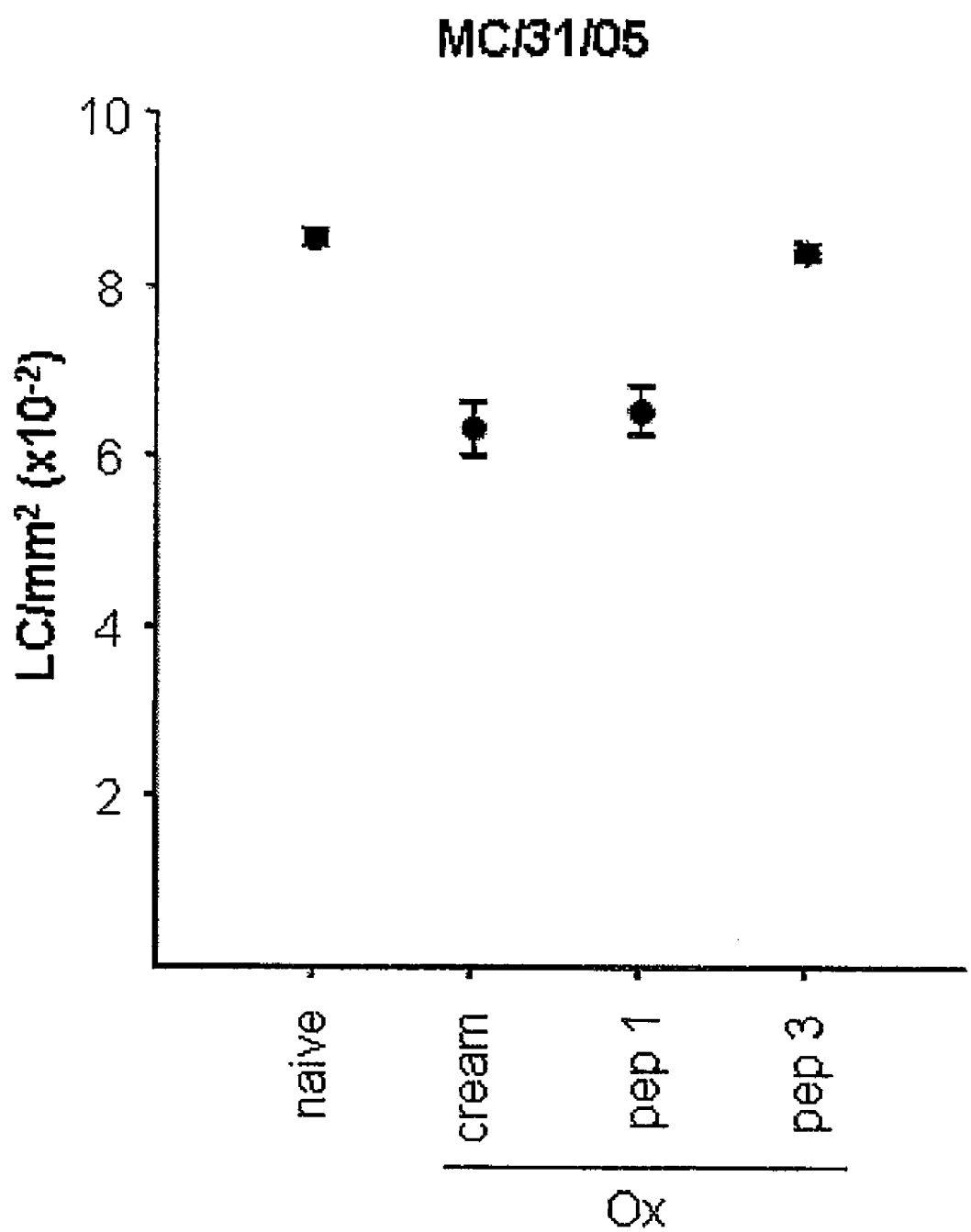

FIG. 3 Epidermal Langerhans cell migration—comparative experiment peptide 1 v. peptide 3.

Figure 4:
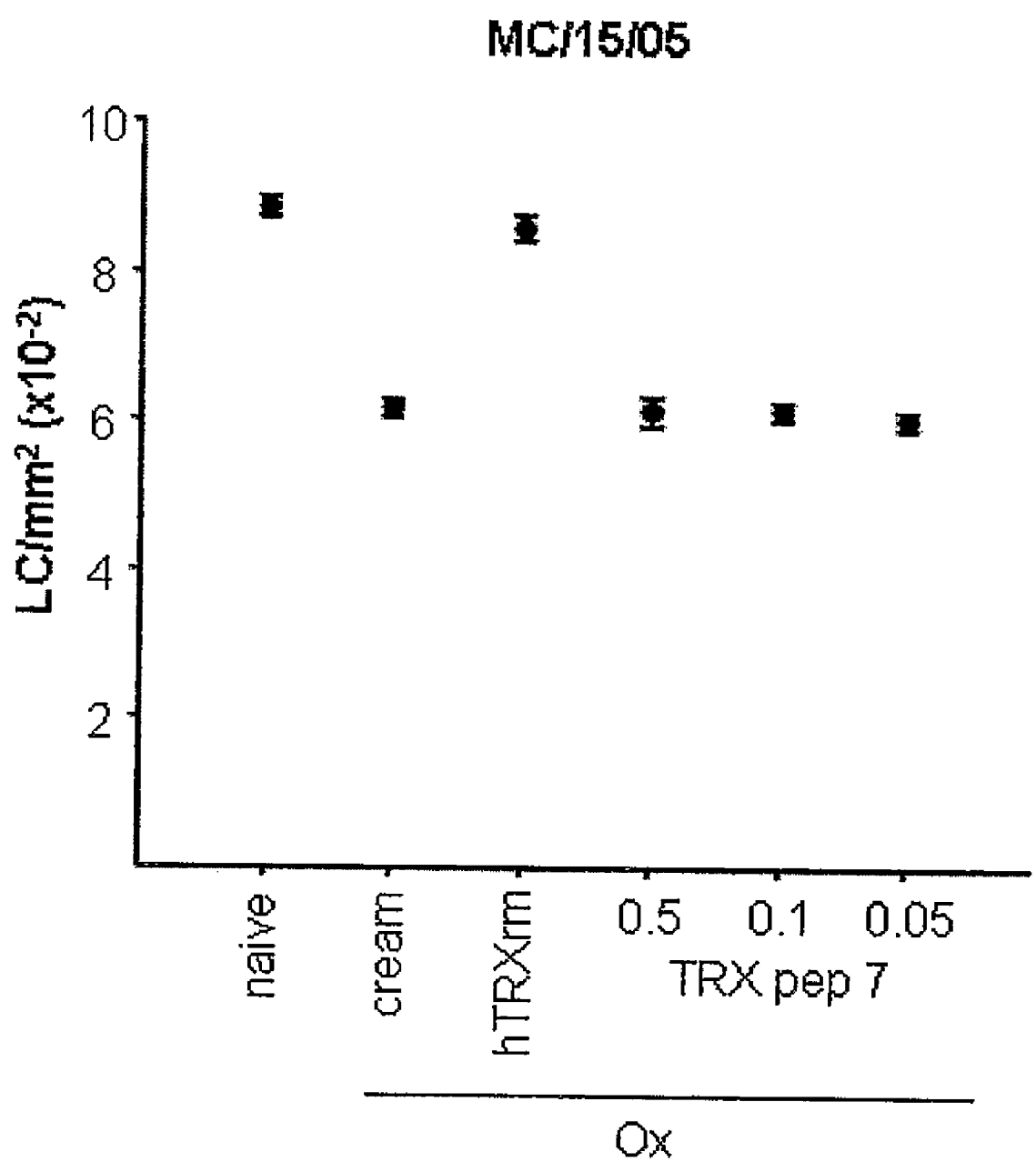

FIG. 4 Epidermal Langerhans cell migration—dose response experiment for peptide 7.

Figure 5:
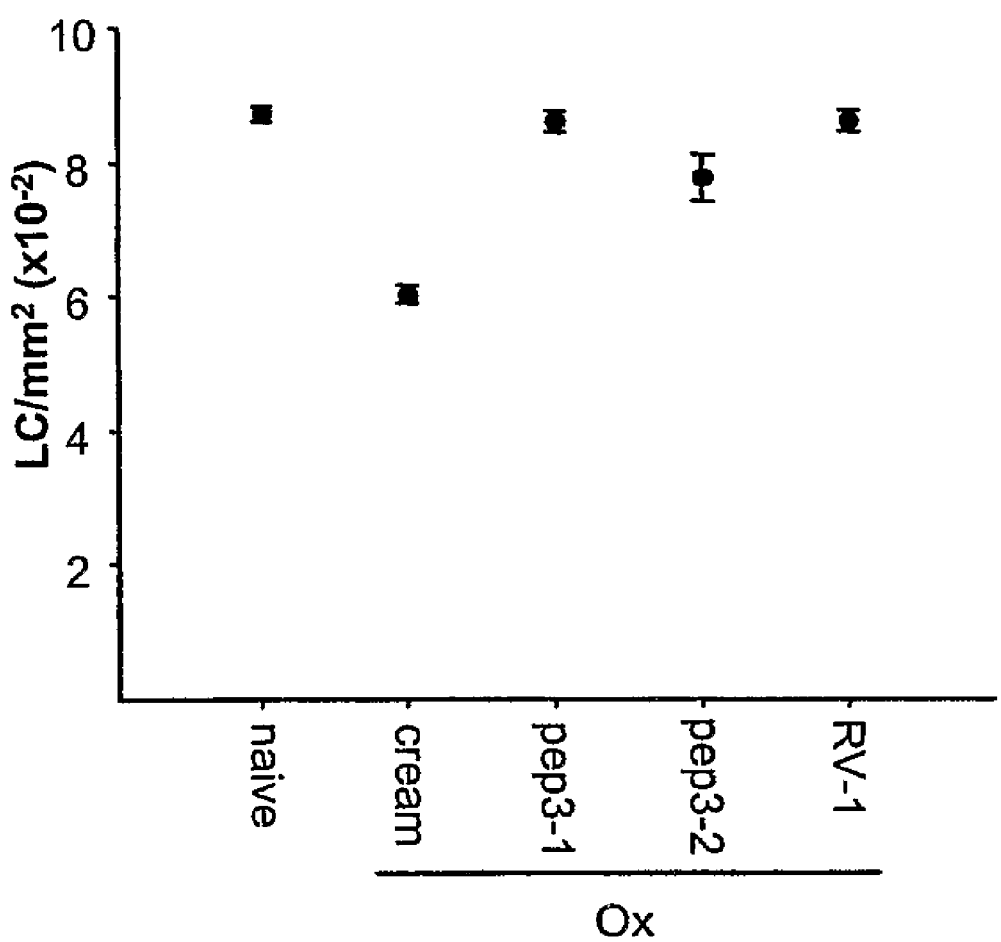

FIG. 5 Epidermal Langerhans cell migration—two independent preparations of peptide 3 (3-1 and 3-2) and peptide RV-1.

Figure 6:
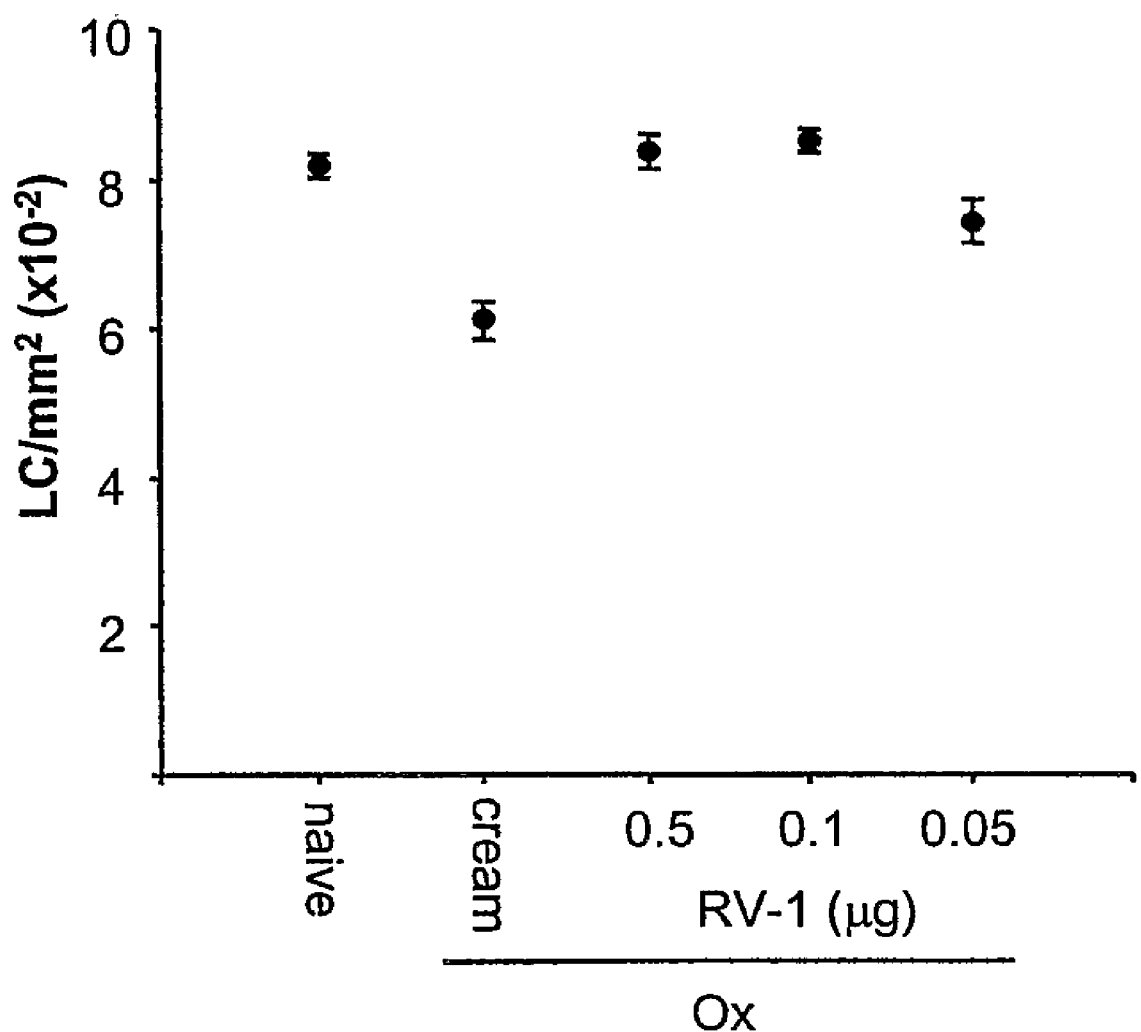

FIG. 6 Epidermal Langerhans cell migration—dose response experiment for peptide RV-1.

Figure 7:
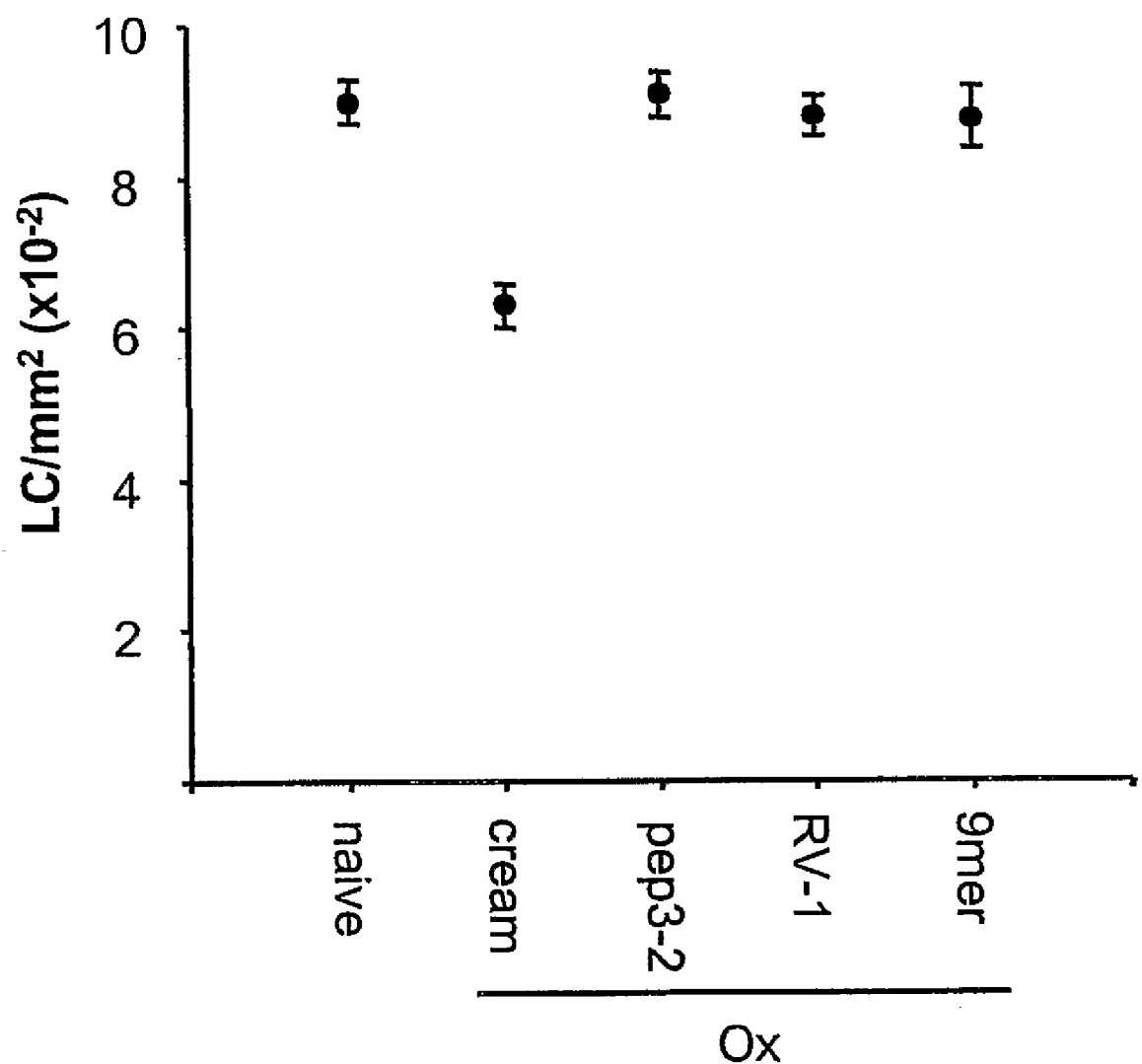

FIG. 7 Epidermal Langerhans cell migration—comparative experiment showing activity of peptide 3, peptide RV-1 and the 9-mer (CGPCKMIKP; SEQ ID NO: 9).

Figure 8:
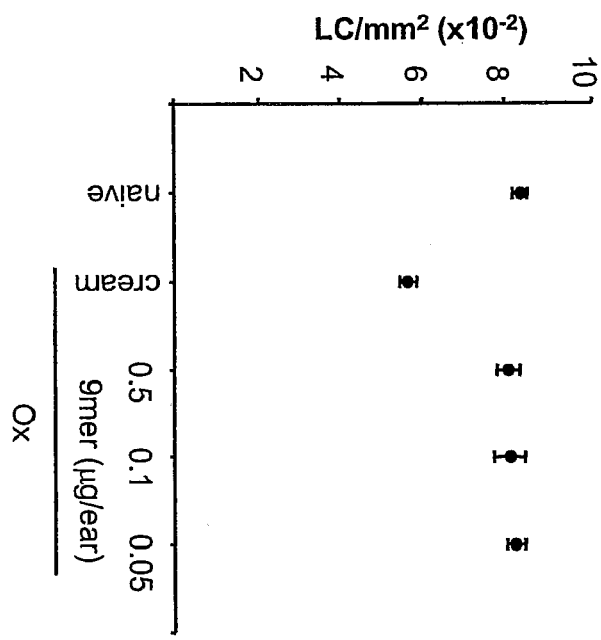
Figure 8:
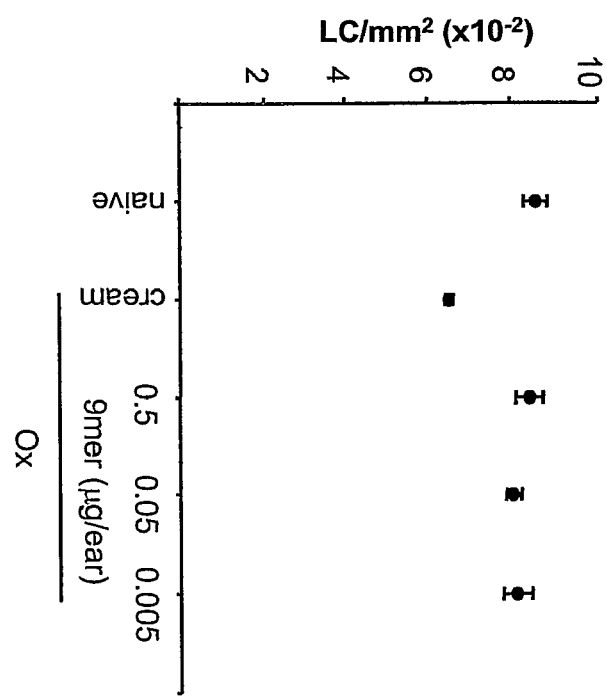

FIG. 8 Epidermal Langerhans cell migration—dose response experiment for the 9-mer (CGPCKMIKP; SEQ ID NO: 9).

Figure 9:
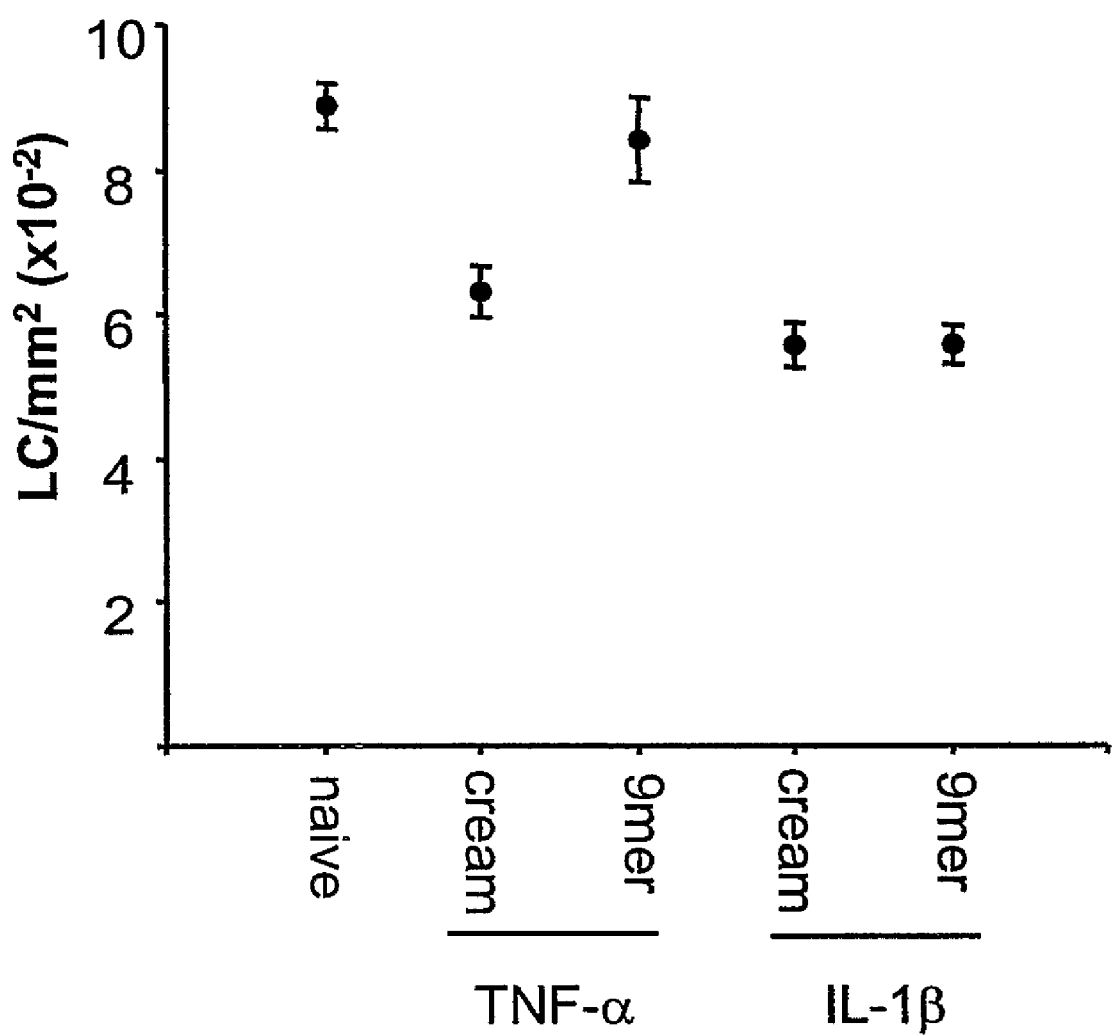

FIG. 9 Epidermal Langerhans cell migration—experiment to investigate whether the 9-mer peptide (CGPCKMIKP; SEQ ID NO: 9) affects Langerhans cell migration induced by either IL-1β or TNF-α.

Figure 10:
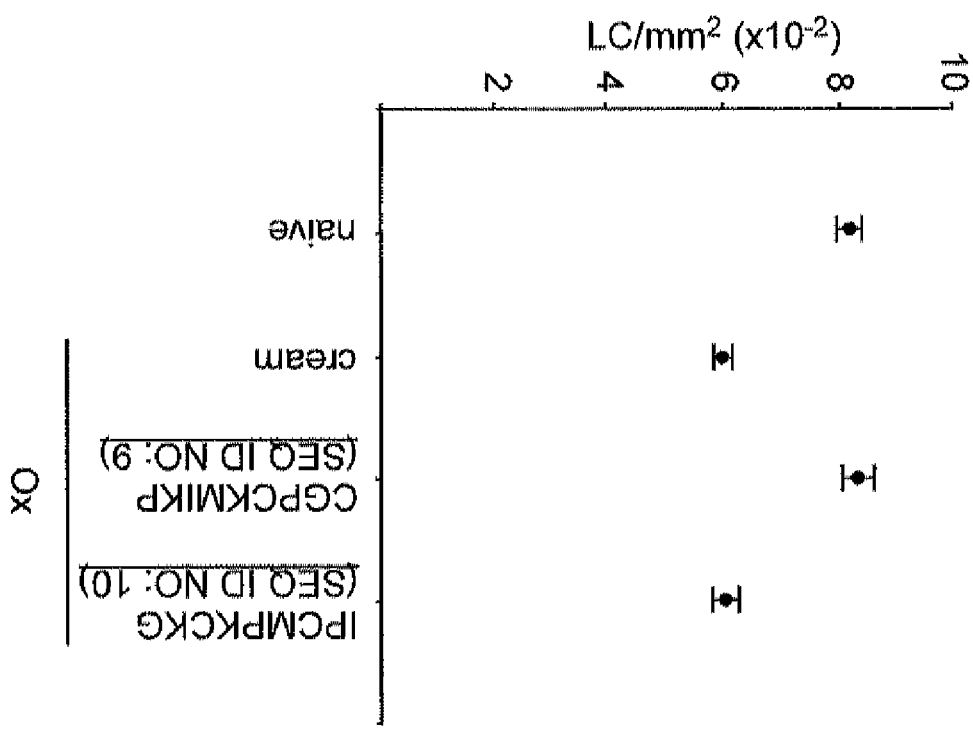
Figure 10:
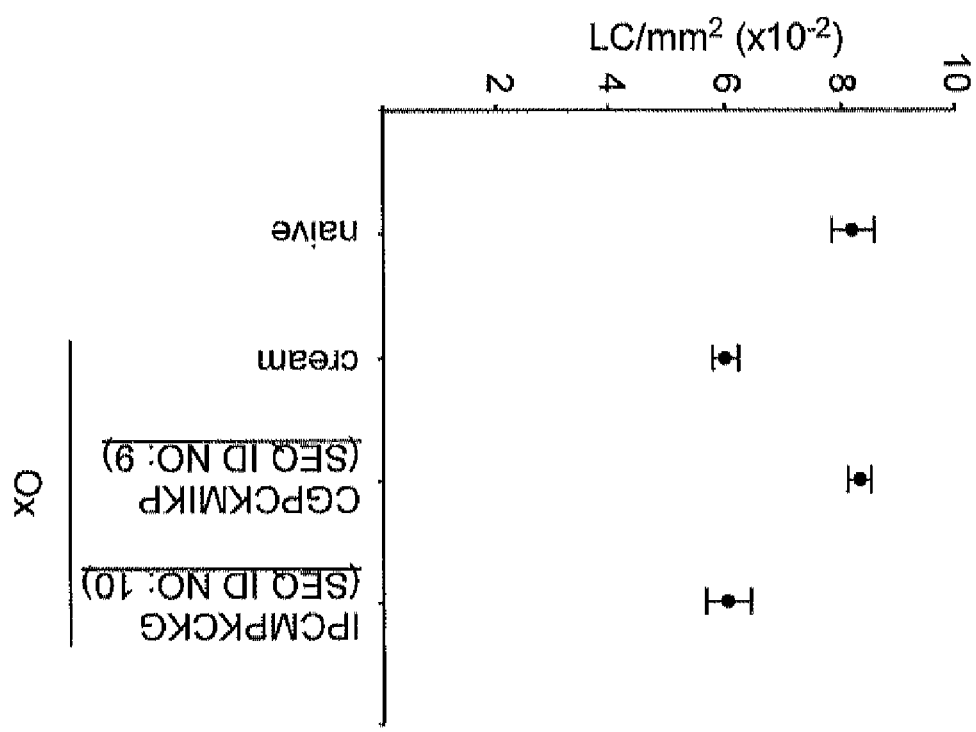

FIG. 10 Epidermal Langerhans cell migration—control experiment showing the activity of the 9-mer (CGPCKMIKP; SEQ ID NO: 9) and a "scrambled" 9-mer (IPCMPKCKG; SEQ ID NO: 10).

Figure 11:
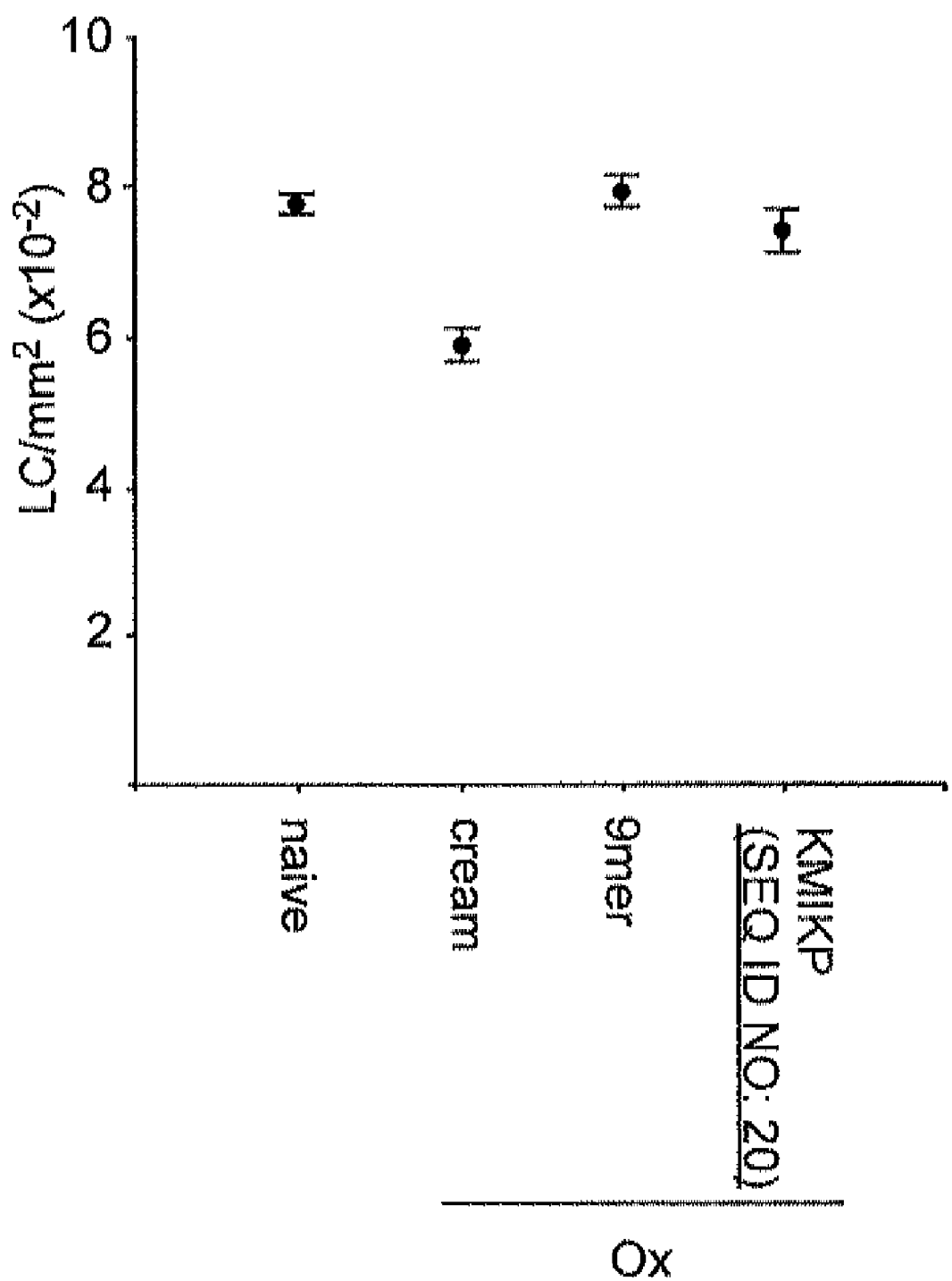

FIG. 11 Epidermal Langerhans cell migration—comparative experiment showing the activity of the 9-mer (CGPCKMIKP; SEQ ID NO: 9) and the KMIMP (SEQ ID NO: 21) peptide.

Figure 12:
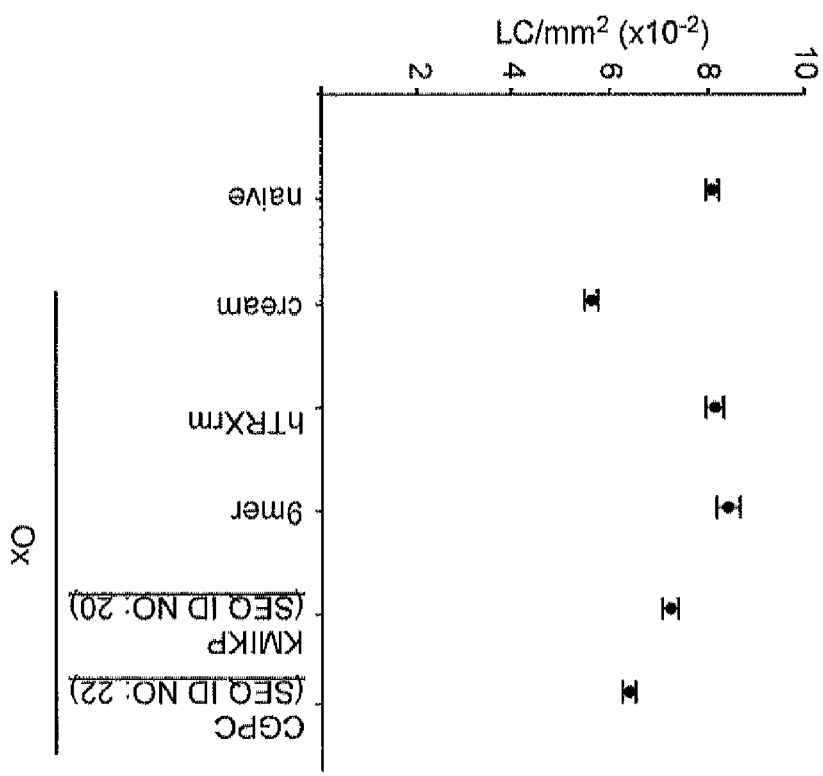
Figure 12:
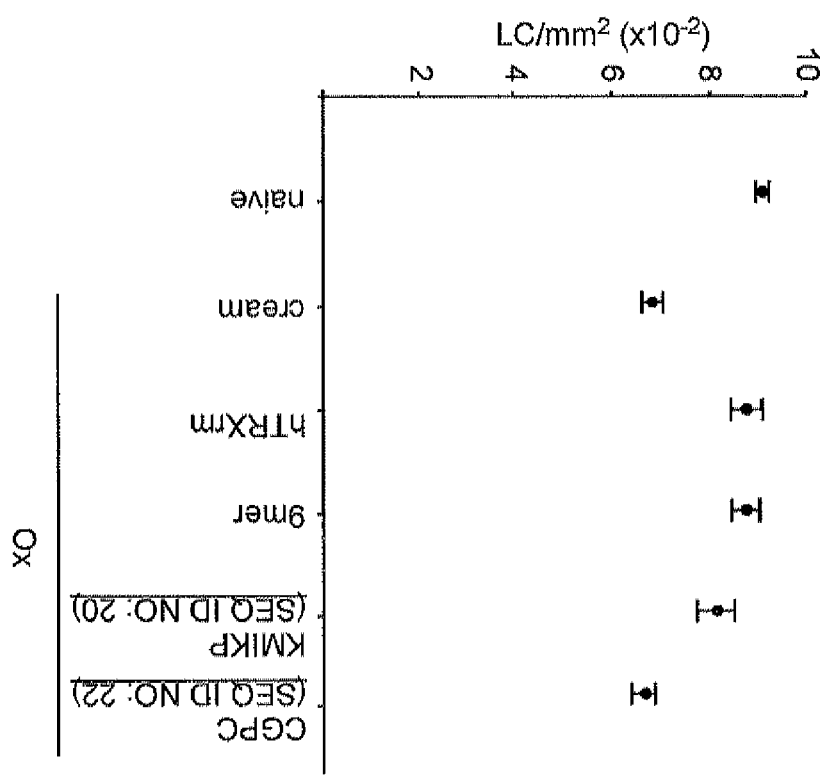

FIG. 12 Epidermal Langerhans cell migration—comparative experiment showing the activity of human thioredoxin (SEQ ID NO. 14), the 9-mer peptide (CGPCKMIKP; SEQ ID NO: 9), the KMIKP (SEQ ID NO: 20) peptide and the CGPC (SEQ ID NO: 22) peptide.

Figure 13:
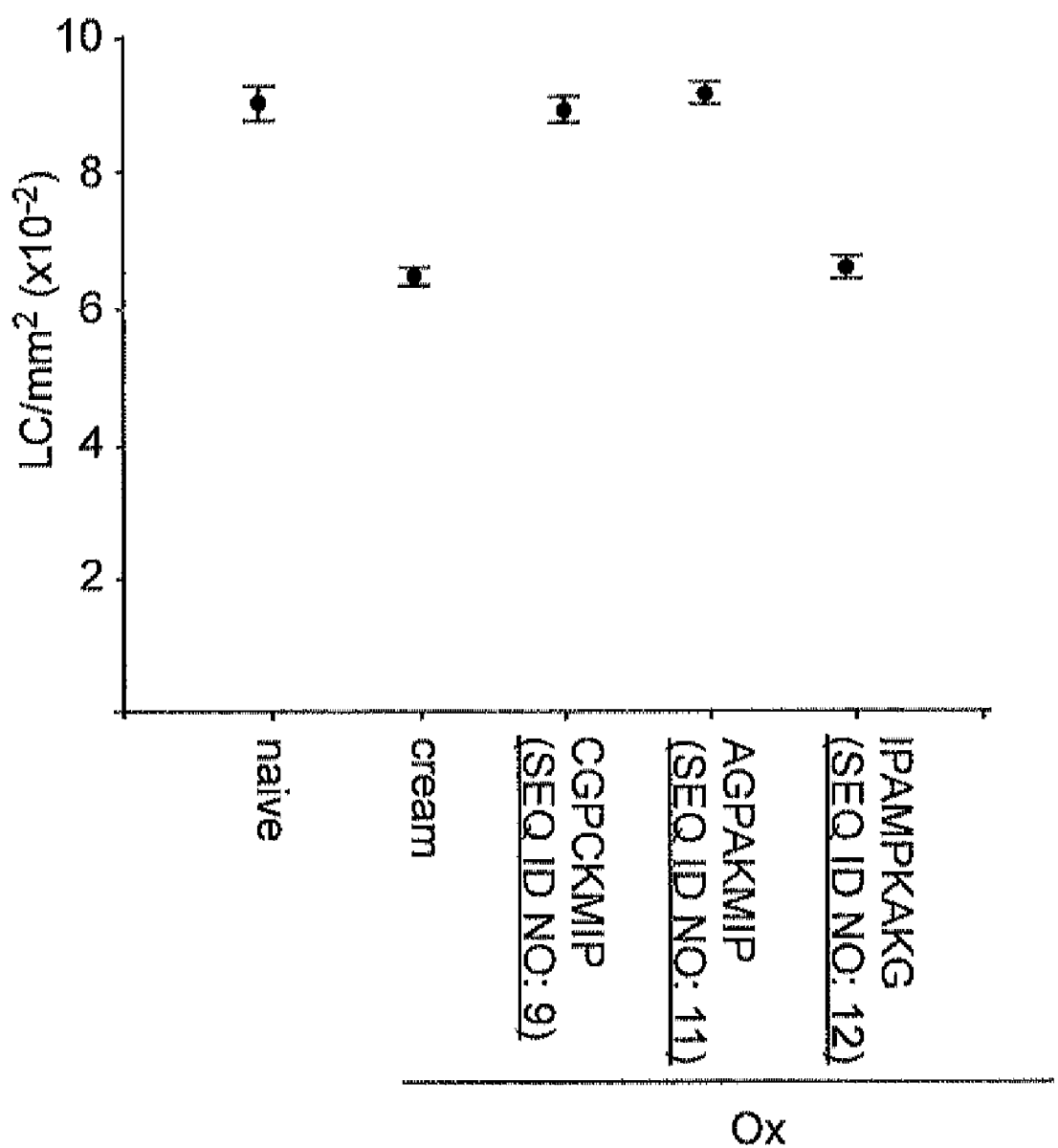

FIG. 13 Epidermal Langerhans cell migration—comparative experiment showing the activity of the 9-mer peptide (CGPCKMIKP; SEQ ID NO: 9), a cysteine free "scrambled" 9-mer (IPAMPKAKG; SEQ ID NO: 12) and the cysteine free 9-mer peptide (AGPAKMIKP; SEQ ID NO: 11).

EXAMPLES

The following peptides were chemically synthesised.

```
Peptide 1                        VKQIESKTAFQEALDAAGDK  (SEQ ID NO. 1)

Peptide 2                        AAGDKLVVVDFSATWCGPCK  (SEQ ID NO. 2)

Peptide 3                        CGPCKMIKPFFHSLSEKYSN  (SEQ ID NO. 3)

Peptide 4                        EKYSNVIFLEVDVDDCQDVA  (SEQ ID NO. 4)

Peptide 5                        CQDVASECEVKCMPTFQFFK  (SEQ ID NO. 5)

Peptide 6                        FQFFKKGQKVGEFSGANKEK  (SEQ ID NO. 6)

Peptide 7                        ANKEKLEATINELV        (SEQ ID NO. 7)

Peptide RV1                      SATYCGPCKMIKP         (SEQ ID NO. 8)

9-mer peptide                    CGPCKMIKP             (SEQ ID NO. 9)

Scrambled 9-mer                  IPCMPKCKG             (SEQ ID NO. 10)

Cysteine free 9-mer              AGPAKMIKP             (SEQ ID NO. 11)

Scrambled cysteine free 9-mer    IPAMPKAKG             (SEQ ID NO. 12)

"KMIKP"                          KMIKP                 (SEQ ID NO: 20)
```

Recombinant human thioredoxin (rhTRX) (SEQ ID NO. 14) is also included in some of the experiments.

(SEQ ID NO. 14)
MVKQIESKTAFQEALDAAGDKLVVVDFSATWCGPCKMIKPFFHSLSEKYS

NVIFLEVDVDDCQDVASECEVKCMPTFQFFKKGQKVGEFSGANKEKLEAT

INELV

Various tissue studies are conducted to examine the effect of each of the aforementioned polypeptides on allergen (oxazolone) induced Langerhans Cell (LC) migration. Applications are in μg unless otherwise stated.

Experiment 1

The purpose of this experiment is to determine whether topical application of peptide 1 is able to influence the integrity of LC migration induced by subsequent exposure at the same site to oxazolone, a potent contact allergen known to cause the mobilization of LC. The results of a representative experiment are illustrated in FIG. 1. The results reveal that prior exposure to peptide 1 does not inhibit allergen-induced LC migration.

Experiment 2

The purpose of this experiment is to determine whether topical application of peptide 3 is able to influence the integrity of LC migration induced by subsequent exposure at the same site to oxazolone. The results of three independent experiments are illustrated in FIG. 2. The results reveal that prior exposure to peptide 3 in each instance causes a complete (or near complete) inhibition of allergen-induced LC migration at the highest concentration (0.5 μg) tested. In two of the three experiments there is some indication for a dose-related inhibition of allergen-induced LC migration by peptide 3. The conclusion drawn is that topically applied peptide 3 is able to inhibit one or more biological processes required for the effective mobilization and migration of LC in response to a stimulus, in this instance the contact allergen oxazolone.

Experiment 3

The purpose of this experiment is to conduct a simultaneous comparative analysis of peptide 1 and peptide 3. The results of the experiment are illustrated in FIG. 3—and confirm the findings of the previous experiments. That is, that prior exposure to peptide 3 causes a substantial inhibition of allergen-induced LC migration, whereas identical prior exposure to peptide I does not inhibit allergen-induced LC migration.

Experiment 4

The purpose of this experiment is to determine whether topical application of peptide 7 is able to influence the integrity of LC migration induced by subsequent exposure at the same site to oxazolone. The results of a representative experiment are illustrated in FIG. 4. The results reveal that prior exposure to peptide 7 does not inhibit allergen-induced LC migration.

Experiment 5

The purpose of this experiment is to determine whether there is any variation in activity between peptide synthesis batches (pep3-1 and pep-3-2) and also to test the activity of peptide RV-1. The results of a representative experiment are illustrated in FIG. 5. The results reveal that prior exposure to peptide RV-1 does inhibit allergen. induced LC migration—and that only a small variation in activity is observed between peptide synthesis batches.

Experiment 6

The purpose of this experiment is to examine the dose-response of peptide RV-1. The results of a representative experiment are illustrated in FIG. 7.

Experiment 7

The purpose of this experiment is to compare the activity of peptide 3, peptide RV-1 and the 9-mer (CGPCKMlKP; SEQ ID NO: 9). The results of a representative experiment are illustrated in FIG. 7. These results show that all of the peptides tested are active.

Experiment 8

The purpose of this experiment is to examine the dose response of the 9-mer peptide (CGPCKMIKP; SEQ ID NO: 9). The results of a representative experiment are illustrated in FIG. 8. The results of the experiment confirm the activity of the 9-mer peptide at all doses tested.

Experiment 9

The purpose of this experiment is to investigate whether the 9-mer peptide (CGPCKMIKP; SEQ ID NO: 9) could affect Langerhans Cell migration induced by either IL-1β or TNF- α. The results of a representative experiment are illustrated in FIG. 9. These results reveal that prior topical exposure to the 9-mer peptide is able to cause an almost complete inhibition of Langerhans Cell migration induced by the intradermal (id) injection of homologous TNF-α. In contrast, the 9-mer peptide applied in the same way is without influence on the integrity of Langerhans Cell migration provoked by id administration of homologous IL-1β. The interpretation is that topical administration of the 9-mer peptide is associated with a perturbation of IL-1β function.

Experiment 10

The purpose of this control experiment is to examine the activity of the 9-mer (CGPCKMIKP; SEQ ID NO: 9) and a control "scrambled" 9-mer (IPCMPKCKG; SEQ ID NO: 10). The results of a representative experiment are illustrated in FIG. 10. The results show that the order of the amino acids in the 9-mer peptide is important in order to retain biological activity—since the scrambled 9-mer, which comprises the same amino acids as the 9mer, is not biologically active.

Experiment 11

The purpose of this experiment is to confirm the activity of the 9-mer (CGPCKMIKP; SEQ ID NO: 9) and examine the activity of the peptide KMIMP (SEQ ID NO: 21)—which is shown to be active. The results of a representative experiment are illustrated in FIG. 11.

Experiment 12

The purpose of this comparative experiment is to show the activity of recombinant human thioredoxin (hTRX) (SEQ ID NO. 14), from which the peptides of the present invention are derived, the 9-mer peptide (CGPCKMIKP; SEQ ID NO: 9), the KMIKP (SEQ ID NO: 20) peptide and the CGPC (SEQ ID NO: 22) peptide. All peptides were applied in equimolar doses (1.38 μM)—which equates to 0.5 μg hTRX, 0.04 μg of the 9-mer peptide, 0.025 μg of the KMIKP (SEQ ID NO: 20) peptide and 0.016 μg of the CGPC (SEQ ID NO: 22) peptide. The results of a representative experiment are illustrated in FIG. 12—where it can be seen that all but the CGPC (SEQ ID NO: 22) peptide appear to exhibit biological activity.

Experiment 13

The purpose this experiment is to compare the activity of the 9-mer peptide (CGPCKMIKP; SEQ ID NO: 9), a control cysteine free "scrambled" 9-mer (IPAMPKAKG; SEQ ID NO: 12) and the cysteine free 9-mer peptide (AGPAKMIKP; SEQ ID NO: 11). The results of a representative experiment are illustrated in FIG. 13—where it can be seen that the 9-mer peptide (CGPCKMIKP; SEQ ID NO: 9) and the cysteine free 9-mer peptide (AGPAKMIKP; SEQ ID NO: 11) are active whereas the control cysteine free "scrambled" 9-mer is not.

What is claimed is:

1. A peptide comprising the amino acid sequence KMIKP (SEQ ID NO: 20), wherein the peptide consists of no more than 10 amino acids and wherein the peptide is capable of inhibiting allergen induced Langerhans cell migration.

2. A peptide according to claim 1, wherein the peptide comprises an amino acid sequence selected from the group consisting of SEQ ID NO: 9 and SEQ ID NO: 11.

3. A pharmaceutical composition comprising a peptide according to claim 1 or 2.

4. A pharmaceutical composition according to claim 3, wherein the composition is selected from the group consisting of a solution, a gel, a lotion, an ointment, a cream and a paste.

5. A peptide according to claims 1 or 2 for use as a pharmaceutical.

6. A method of treating an inflammatory skin condition, the method comprising:
   (i) providing a composition comprising a peptide comprising the amino acid sequence KMIKP (SEQ ID NO: 20), wherein the peptide consists of no more than 10 amino acids, and wherein the peptide is capable of inhibiting allergen induced Langerhans cell migration; and
   (ii) topically applying the composition to the skin of a subject in need thereof.

7. A method according to claim 6, wherein said inflammatory skin condition is selected from the group consisting of psoriasis, lichen planus, atopic eczema, irritant or allergic contact dermatitis, contact urticaria, infantile eczema and acne vulgaris.

8. A peptide according to claim 1, wherein the peptide consists of an amino acid sequence selected from the group consisting of SEQ ID NO: 9; SEQ ID NO: 11; and SEQ ID NO: 20.

9. A method according to claim 6, wherein the peptide comprises an amino acid sequence selected from the group consisting of SEQ ID NO: 9; SEQ ID NO: 11; and SEQ ID NO: 20.

10. A method according to claim 6, wherein the peptide consists of an amino acid sequence selected from the group consisting of SEQ ID NO: 9; SEQ ID NO: 11; and SEQ ID NO: 20.

11. A method according to claim 10, wherein the peptide consists of amino acid sequence SEQ ID NO: 9.

12. A method according to claim 10, wherein the peptide consists of amino acid sequence SEQ ID NO: 11.

13. A method according to claim 10, wherein the peptide consists of amino acid sequence SEQ ID NO: 20.

* * * * *